United States Patent [19]

Miller

[11] Patent Number: 4,980,901

[45] Date of Patent: Dec. 25, 1990

[54] APPARATUS FOR AND METHODS OF DETECTING COMMON EXPLOSIVE MATERIALS

[75] Inventor: Robert B. Miller, Albuquerque, N. Mex.

[73] Assignee: The Titan Corporation, San Diego, Calif.

[21] Appl. No.: 242,350

[22] Filed: Sep. 9, 1988

[51] Int. Cl.$^5$ .......................................... G01N 23/223
[52] U.S. Cl. ....................................... 378/45; 378/53; 378/57
[58] Field of Search ......................... 378/1, 45, 53, 57

[56] References Cited

U.S. PATENT DOCUMENTS

| | | | |
|---|---|---|---|
| 3,662,882 | 5/1972 | Obermayer | 378/45 |
| 3,701,899 | 10/1972 | Voparil | 378/45 |
| 4,031,388 | 6/1977 | Morita et al. | 378/45 |
| 4,415,804 | 11/1983 | Sowerby | 378/53 |

Primary Examiner—Craig E. Church
Attorney, Agent, or Firm—Ellsworth R. Roston; Charles H. Schwartz

[57] ABSTRACT

A beam of energy in a first form, such as electrons, is provided in a first direction. The beam may be pulsed or continuous. The beam is intercepted by a member, such as a converter target, to produce energy in a second form such as x-rays. The converter target may be formed from a heavy material such as tungsten or tantalum. The interaction of the electron beam with the converter target will produce energetic bremsstrahlung x-rays in an energy range including 10.6 Mev to approximately 13.0 Mev. This range is sufficient to excite the abundant nitrogen atoms in common explosives to induce the production of annihilation photons but is not sufficient to substantially excite atom of the most abundant elements of the earth's crust (e.g. oxygen, silicon, iron, aluminum, carbon, hydrogen, etc.), which comprise most common fabricated articles and soils. The converter target is disposed relative to an object (e.g. a suitcase in an airport) to obtain the production of energy in a third form, such as photons, from the object. The photons pass to a detector such as a scintillation counter which determines the concentration of the nitrogen in the object. The detector may be gated so as to be activated only when the photons are passing from the object to the detector. When the object is a suitcase which is moved along a conveyor, the detector may be downstream from the source in the direction of movement of the conveyor.

37 Claims, 3 Drawing Sheets

FIG. 2

COMPOSITION OF MILITARY AND COMMERCIAL EXPLOSIVES

| COMPOUND | DENSITY (gm/cm$^3$) | WT.% C | H | N | O | Pb |
|---|---|---|---|---|---|---|
| RDX (CLYCLOTRIMETHYLENE-TRINITRAMIN) | 1.8 | 16.2 | 2.7 | 37.8 | 43.2 | -- |
| TNT (TRINITROTOLUENE) | 1.6 | 37.0 | 2.2 | 18.5 | 42.2 | -- |
| AN (AMMONIUM NITRATE) | 1.5 | -- | 5.0 | 35.0 | 60.0 | -- |
| Pb AZIDE | 4.8 | -- | -- | 29.0 | -- | 61.0 |
| Pb STYPHNATE | 3.0 | 16.6 | 0.2 | 0.7 | 25.8 | 48.0 |
| HMX (CYCLOTETRAMETHYLENE-TETRANITRAMINE) | 2.0 | 18.2 | 3.0 | 42.4 | 36.4 | -- |
| NG (NITROGLYCERINE) | 1.6 | 15.9 | 2.2 | 18.5 | 63.4 | -- |
| EGDN (ETHYLENEGLYCOLDINITRATE) | 1.4 | 15.8 | 2.6 | 18,4 | 63.2 | -- |
| PETN (PENTAERITHRITAL-TETRANITRATE) | 1.75 | 15.7 | 2.6 | 18.4 | 63.2 | -- |

DENSITY AND COMPOSITION OF MATURAL MATERIALS

| MATERIAL | DENSITY (gm/cm$^3$) | WT.% C | H | N | O |
|---|---|---|---|---|---|
| WOOD | 1 | 44.0 | 6.2 | LOW | 49.0 |
| WATER | 1 | -- | 11.0 | -- | 89.0 |
| SOIL | 1.1-1.5 | LOW | 0.1-6 | LOW | HIGH |
| ROCKS | 2-3 | LOW | -- | LOW | HIGH |

FIG. 3

APPARATUS FOR AND METHODS OF DETECTING COMMON EXPLOSIVE MATERIALS

This invention relates to apparatus for, and methods of, measuring the concentration of nitrogen in an object for the purpose of detecting explosives. More particularly, the invention relates to apparatus for, and methods of, preferentially measuring the concentration of nitrogen in an object while minimizing the simultaneous detection of other elements in common articles or soil having a density similar to that of the object being detected.

Most explosives contain a considerable concentration of nitrogen as one of the elements in the explosives. Objects containing explosives are detected by determining the amount of nitrogen in such objects. However, the explosives also contain other common elements. These elements include carbon, hydrogen and oxygen. Many explosives also have densities similar to the densities of the earth's soil.

One problem with detectors of the prior art has been that the elements such as carbon, hydrogen and oxygen create noise in such detectors and such noise masks the signals obtained from the nitrogen in the explosives. Furthermore since soil has a density similar to that of the object being detected, the soil inhibits the detection of nitrogen in the equipment of the prior art.

The detection of explosives is becoming of increasing importance. For example, the detection of explosives is important at airports to prevent sabotage and highly explosive materials from being illegally transported. The detection of explosives in the ground is also important in times of warfare to obtain the removal of mines located below the earth's surface. Such detection also has importance in a subsequent peace to prevent mines with delayed activation from becoming effective. The problem relating to the detection of explosives has been in existence for some time. Serious efforts have been made to resolve this problem. In spite of this, a full resolution of the problem has not been made. g This invention provides apparatus for, and methods of, detecting the concentration of nitrogen in objects while minimizing background noise from common elements such as carbon, oxygen and hydrogen and from soil having a density similar to that of the object being detected. The apparatus and methods of this invention are also able to detect the concentration of nitrogen in objects such as suitcases while the suitcases are conveyed as on a belt past a detector.

In one embodiment of the invention, a beam of energy in a first form, such as electrons, is provided in a first direction. The beam may be pulsed or continuous. The beam is intercepted by a member, such as a converter target, to produce energy in a second form such as x-rays. The converter target may be formed from a heavy material such as tungsten or tantalum.

The interaction of the electron beam with the converter target will produce energetic bremsstrahlung x-rays in an energy range to approximately 13.0 Mev. This range is sufficient to excite the abundant nitrogen atoms in common explosives to induce the production of photons but is not sufficient to substantially excite atoms of other common materials (e.g. oxygen, silicon, aluminum, iron, carbon and hydrogen) which comprise most fabricated articles and soils.

The x-rays in the range of approximately 10.6 Mev to approximately 13 Mev undergo a photonuclear reaction with the nitrogen atoms in the explosive and thereby cause radioactive nitrogen atoms to be produced. The radioactive nitrogen atoms decay by emitting positrons which immediately interact with available electrons to produce pairs of 0.511 Mev annihilation radiation photons These photons are detected to indicate the pressure of significant amounts of nitrogen in the explosive.

The converter target is disposed relative to an object (e.g. a suitcase in an airport) to obtain the production of energy in a third form, such as the photons described in the previous paragraph, from the object. The photons pass to a detector such as a scintillation counter which determines the concentration of the nitrogen in the object The detector may be gated so as to be activated only when the photons are passing from the object to the detector When the object is a suitcase which is moved along a conveyor, the detector may be downstream from the source in the direction of movement of the conveyor.

In the drawings:

FIG. 2 is a table showing the density and composition of various common explosives;

FIG. 3 is a table showing the density and composition of several different materials commonly occurring in the earth's surface;

Figure 1:
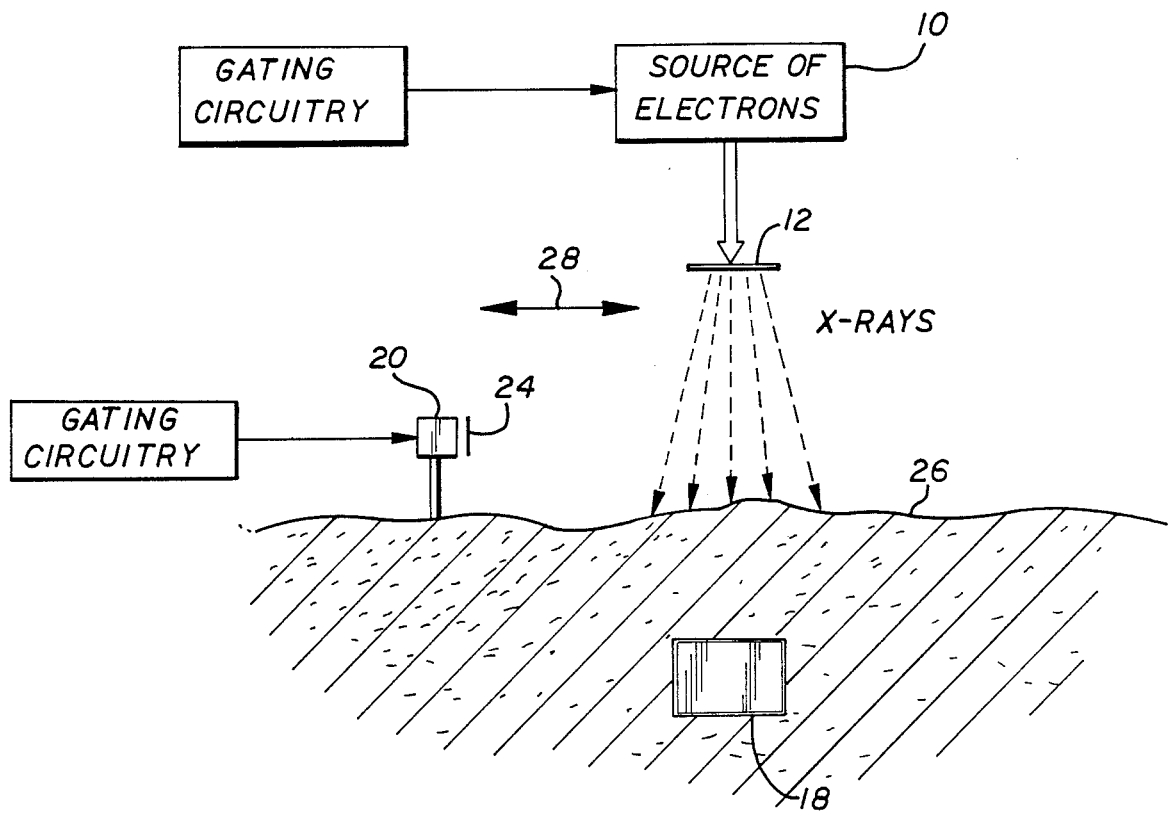
FIG. 1 is a schematic view partly in block form to show electrical features, of apparatus constituting one embodiment of the invention for detecting the concentration of nitrogen in various objects buried in the soil.

In one embodiment of the invention, apparatus 10 is provided for producing a first form of energy. The apparatus 10 may be constructed to produce electrons and to accelerate the electrons in a beam toward a x-ray converter target 12. The apparatus 10 may be gated in a conventional manner by circuitry 14 to produce the electron beam only periodically. The spot size of the electron beam and the angle of incidence of the beam on the converter target 12 may be controlled to provide coverage of the x-ray beam over a particular surface area of the earth 26. The apparatus 10 may be constructed in a manner conventional in the prior art.

The converter target 12 may be constructed to produce energy in a second form different from the first form of energy.

For example, the converter target 12 may be constructed from heavy material, such as tungsten or tantalum having a high atomic number to provide bremsstrahlung x-rays. The bremsstrahlung x-rays may have a particular range of energies such as to approximately twelve and one half million electron volts (12.5 Mev).

The range of x-ray energies from the converter target 12 has certain important advantages It includes the energy of at least approximately ten and six tenths million electron volts (10.6 Mev) for obtaining the production of photons from nitrogen atoms. However, it is below the threshold energy for obtaining the production of annihilation photons via photoneutron reactions from elements such as carbon, silicon, aluminum, iron, oxygen and hydrogen found in some concentration in common objects (including explosives) to be interrogated. It is also substantially below the threshold energy of obtaining the production of annihilation photons in a similar process from the elements commonly found in the earth's crust. Because of this, the energy from the converter target 12 is sufficiently high to activate the nitrogen atoms in an object 18 being detected without activating the atoms of other commonly appearing elements in the earth's crust or most explosives.

The x-rays from the converter target 12 are dissipated by Compton scattering and pair production interactions with the soil material when the object 18 to be detected is disposed below the surface 26 of the earth. Compton scattering occurs when a gamma ray impinges upon an atom and produces an electron and another gamma ray. Pair production occurs when a gamma ray impinges upon an atom and produces an electron and a positron. When pair production occurs electrons and positrons may combine to produce two (2) photons of a characteristic energy such as 0.511 Mev. This is designated as annihilation photon production The production of photons by annihilation production is used in this invention.

The object 18 is disposed relative to the converter target 12 to receive the x-rays from the converter target and to provide for the production of photons from the nitrogen in the object. The production of photons is obtained by the conversion of $N^{14}$ nitrogen atoms to radioactive $N^{13}$ nitrogen atoms through a photonuclear reaction. The $N^{13}$ atoms subsequently decay by positron emission, which results in annihilation photon production. A detector 20 is disposed relative to the object 18 to detect the photons from the nitrogen in the object 18 and to indicate the concentration of the nitrogen in the object from such photon detection. The detector 20 may constitute a scintillation counter made from a suitable material such as bismuth germanate or sodium iodide.

The detector 20 is disposed relative to the source 12 and the object 18 to detect the energetic photons from the nitrogen in the explosive without detecting the energetic photons produced by Compton scattering and pair production. The detector 20 may be gated in a conventional manner as by circuitry 22 so as to be activated only at periods of time consistent with the periodic production of the electron beam by the apparatus 10. The detector 20 may additionally be shielded as at 24 to enhance the isolation of the detector from the converter target 12.

The photons are produced from the nitrogen atoms in the object 18 as a result of the activation of the nuclei of the nitrogen atoms by the x-rays from the source 12. The activated nuclei of the nitrogen atoms then decay with a half life of approximately ten (10) minutes by isotropically emitting positrons The positrons combine with electrons in an annihilation process to obtain the production of two (2) photons with an energy level of 0.511 Mev. Although these photons may be attenuated by Compton scattering and photoelectric interactions in the ground when the object 18 is disposed in the ground, a substantial number of the photons escape into the atmosphere for detection by the detector 20.

When the object 18 is an explosive such as a mine disposed below the surface 26 of the earth, the apparatus constituting this invention may detect the object with ninety percent (90%) confidence when the object (5-10 kg of RDX explosive, for example) is at a depth of four inches (4") below the earth's surface. The object 18 may be detected by moving the apparatus constituting this invention at a suitable rate such as a speed of approximately three miles per hour (3 mph) along the earth's surface. The movement of the apparatus constituting this invention along the earth's surface is indicated by an arrow designated as 28 in FIG. 1. The apparatus constituting this invention is able to provide such detection by utilizing power at a relatively low level such as approximately fifty kilowatts (50 kw).

FIG. 2 is a table setting forth the composition of various commercial and military explosives. As will be seen, most of these explosives contain a significant concentration of nitrogen by weight However, most of these explosives also contain significant concentrations of other commonly occurring elements such as carbon, hydrogen and oxygen. By preferentially detecting the production of photons from the nitrogen atoms in the object 18 while minimizing any production of photons from the other commonly occurring elements in the explosives, the apparatus minimizes the production of noise signals such as commonly occur with other explosive detectors now in use. Such noise signals may mask the measurements of the concentration of nitrogen in the explosives by the detectors of the prior art.

FIG. 2 also includes a column which indicates the densities of commonly occurring explosives. As will be seen, the densities of such explosives (in grams per cubic centimeter) occur in the range between one (1) and two (2) except for the explosives employing lead, such explosives being quite dense. FIG. 3 shows the relative densities in grams per cubic centimeter ($gm/cm^3$) of various materials commonly occurring on the earth's surface and in the earth's crust.

As will be seen in FIG. 3, water has a density of one (1); soil has a density between one and one tenth (1.1) and one and one half (1.5); and rocks have a density between approximately two (2) and three (3). These densities are similar to the densities of most of the explosives (except those employing lead) shown in FIG. 2 FIG. 3 also shows the concentration by weight of different elements such as carbon nitrogen, oxygen and hydrogen in such commonly occurring materials. The apparatus constituting this invention minimizes any effects of commonly occurring materials such as water, wood, soil and rocks because the energy levels required to obtain photons from such materials are greater than the energy level for obtaining photons from nitrogen and because such apparatus produces energy levels preferentially for the production of photons from nitrogen atoms.

Figure 4:
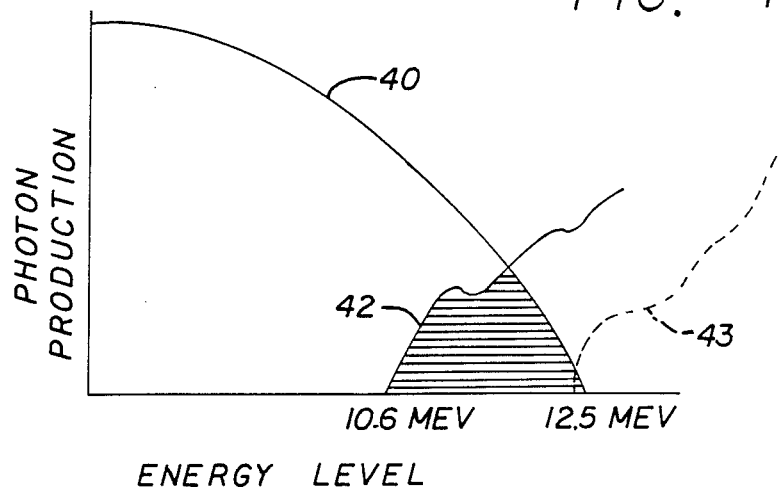
FIG. 4 illustrates curves showing the operation of the apparatus of FIG. 1 and showing the advantages of the apparatus of FIG. 1 over the prior art.

FIG. 4 illustrates curves showing how the apparatus constituting this invention is responsive preferentially to the production of photons from nitrogen atoms In FIG. 4, the horizontal axis indicates x-ray energy and the vertical axis indicates the number of photons produced In FIG. 4, a curve 40 schematically illustrates the number of x-rays produced from the converter target 12 as a function of energy intensity. Curve 42 of FIG. 4 indicates the probability of activating the nitrogen atoms in the object 18, while curve 43 indicates the probability of activating other common atoms. As will be seen by the doubly cross-hatched area, very few photons are produced by atoms which have energy thresholds of approximately twelve and a half million electron volts (12.5 Mev) or higher. As will be seen by the singly cross-hatched area in FIG. 4, the production of photons from nitrogen atoms is significantly enhanced, such photon production occurring at an energy level of approximately ten and six tenths million electron volts (10.6 Mev) or greater.

It will be appreciated that the apparatus discussed above will activate other elements in the soil in addition to nitrogen. However, the abundance of these elements in the soil is generally so low in comparison to the amount of nitrogen in the object being detected that these elements will have relatively little effect on the detection of the nitrogen in the object.

It will also be appreciated that nitrogen is the most abundant element in the atmosphere. For example, nitrogen may comprises about eighty percent (80%) of the gases in the air that human beings breathe. The nitrogen in the atmosphere will cause photons to be produced by the apparatus of this invention in a manner similar to the production of photons from the nitrogen in the object being detected However, the density of the nitrogen in the atmosphere is so low in comparison to the concentration of the nitrogen in the object being detected (e.g. less than 1:1000) that the concentration of the nitrogen in the atmosphere will have little effect on the measurements being made by the apparatus of this invention with respect to the concentration of the nitrogen in such object.

Figure 5:
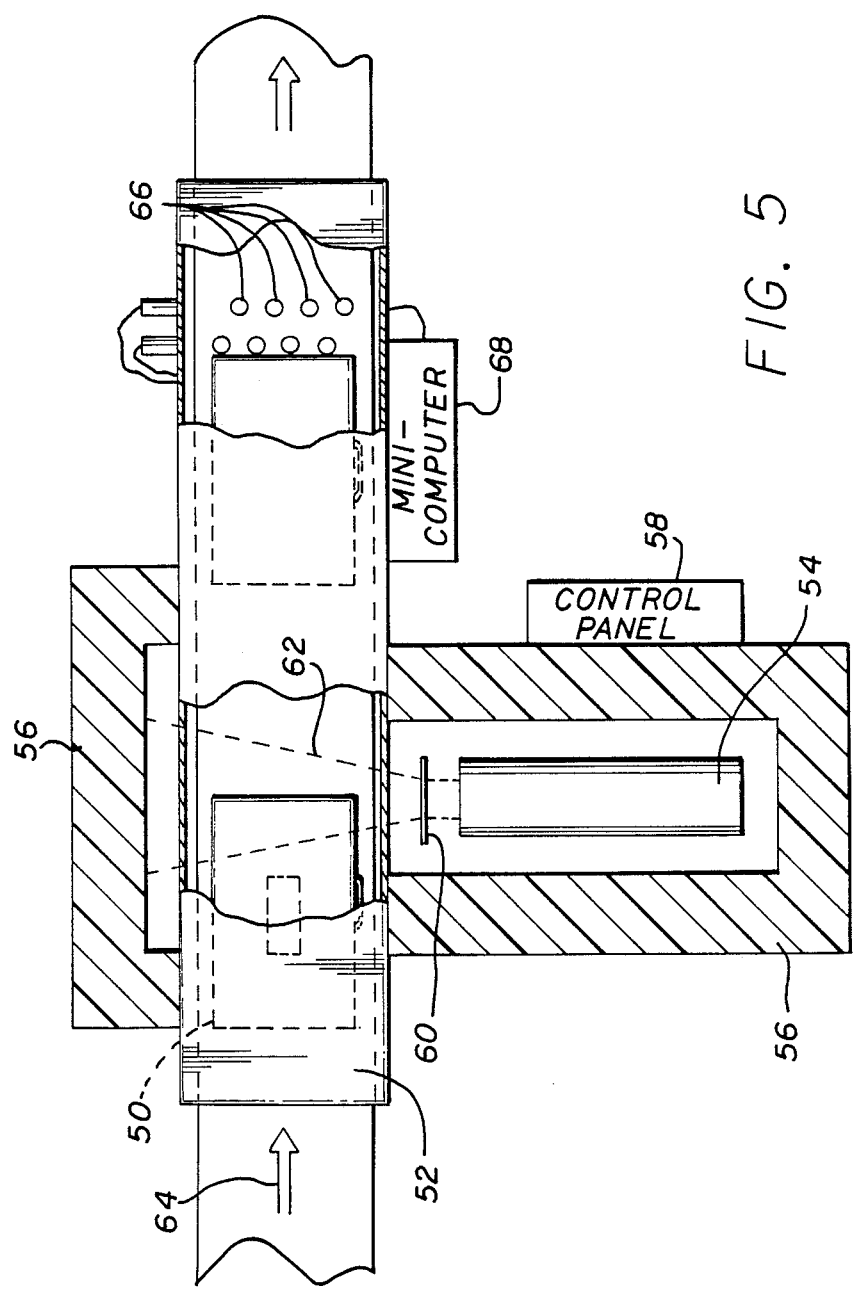
FIG. 5 is a schematic elevational view of another embodiment of the invention for detecting significant concentrations of nitrogen in objects such as suitcases at an airport.

FIG. 5 illustrates apparatus included within the scope of this invention for detecting explosives in objects such as suitcases 50 at an airport. The suitcases 50 are disposed on a conveyor belt 52 in a conventional manner. A source 54 of electrons is disposed within radiation shielding 56 and is controlled by a control panel 58 to direct a controlled flow of electrons to a bremsstrahlung converter target 60. The converter target 60 in turn directs x-rays to the suitcase 50 in an area range indicated by broken lines 62 as the suitcase is moved by the conveyor belt in a direction indicated by an arrow 64. The resultant production of photons from the nitrogen atoms in the suitcase is detected by a counter or counters such as scintillation counters 66. The signals from the scintillation counters 66 are processed by a minicomputer or microproce 68 to provide an indication of the concentration of the nitrogen in the suitcase 50.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

I claim:

1. In combination for determining the presence of explosives by measuring the relative concentration of nitrogen in an objec a converter target made from a material having properties of emitting x-rays, with photons in the x-rays, in a particular energy range of at least approximately 10.6 Mev and of directing such x-rays to the object for the nuclear interreaction of the photons in the x-rays with the nuclei in the nitrogen to obtain the production of annihilation photons while minimizing the production of annihilation photons from other commonly occuring elements in articles or in the earth's crust when the object is disposed in the earth's crust, means for obtaining the emission of the x-rays of at least approximately 10.6 Mev from the converter target to the object, and a detector responsive to the annihilation photons to detect the photons.

2. In a combination as set forth in claim 1, the converter target being made from a material having a high atomic number and the detector being made from a scintillation material.

3. In a combination as set forth in claim 1, the detector being disposed relative to the object to detect substantially only the annihilation photons.

4. In a combination as set forth in claim 1, the particular energy range being between approximately 10.6 Mev and approximately 13.0 Mev.

5. In combination for determining the presence of explosives by measuring the relative concentration of nitrogen in an object, means for producing x-rays, with photons in the x-rays, in a particular range of energies at least as great as that for producing photons from nitrogen atoms but less than that for producing photons from other commonly appearing elements in articles and in the earth's surface to obtain the production of photons substantially only from the nitrogen in the object, the particular range of energies being at least approximately 10.6 Mev, the x-rays being directed to the object for the nuclear interreaction of the photons in the x-rays with the nuclei in the nitrogen to obtain the production of annihilation photons, and means responsive to the annihilation photons for detecting the concentration of the nitrogen in the object.

6. In a combination as set forth in claim 5, wherein the means for producing the x-rays is made from a heavy metal and the detecting means constitutes a scintillation counter.

7. In a combination as set forth in claim 5, the means for producing the x-rays constituting a bremsstrahlung converter target and the photon detector means constituting a scintillation counter.

8. In a combination as set forth in claim 7, the bremsstrahlung x-ray converter target producing energy in a range between approximately 10.6 and approximately 13.0 Mev and the nitrogen in the object having a photonuclear threshold of approximately 10.6 Mev to provide for the production of annihilation photons of approximately 0.511 Mev from the nitrogen.

9. In combination for determining the presence of explosives by measuring the relative concentration of nitrogen in an object, a converter target for producing x-rays, with photons in the x-rays, in a particular range of energy intensities providing for responses by the nitrogen but minimizing responses by other commonly appearing elements, the particular range of energy intensities being at least approximately 10.6 Mev, means for exciting the converter target to obtain the production of the x-rays in the particular range of energy intensities and the direction of such x-rays to the object for the nuclear interreaction of the photons in the x-rays with the nuclei in the nitrogen to obtain the production of annihilation photons, and means responsive to the production of the annihilation photons for indicating the concentration of the nitrogen in the object.

10. In a combination a set forth in claim 9, means for gating the indicating means to respond preferentially to the annihilation photons.

11. In a combination as set forth in claim 10,
the indicating means being constructed to be responsive preferentially to the annihilation photons.

12. In a combination as set forth in claim 11,
the particular range of energy intensities being between approximately 10.6 Mev and approximately 13.0 Mev.

13. In a combination as set forth in claim 10,
the indicating means being disposed relative to the source to be substantially unresponsive to the x-rays from the converter target.

14. In combination for determining the presence of explosives by measuring the relative concentration of nitrogen in an object,
means for providing electrons substantially in a beam,
means responsive to the beam of electrons for producing x-rays, with photons in the x-rays, in a range of energy intensities in which substantially only the nitrogen, among other commonly appearing elements, is responsive to such x-rays to produce annihilation photons, the photons in the x-rays providing a nuclear interreaction with the nuclei in the nitrogen to obtain the production for the annihilation photons, and
means responsive to the annihilation photons to indicate the concentration of the nitrogen in the object.

15. In combination as set forth in claim 14,
means for gating the indicating means to provide an indication substantially only during the time that the annihilation photons pass to the indicating means.

16. In a combination as set forth in claim 14,
means for gating the electron beam means to obtain the production of the electrons in a pulse, and
means for gating the indicating means to provide an indication of the annihilation photons substantially only when such annihilation photons are produced from the nitrogen in such object as a result of the pulse of the electrons from the electron beam means.

17. In a combination as set forth in claim 16,
the indicating means being disposed relative to the electron beam means, the x-ray means and the object to be responsive substantially only the annihilation photons.

18. In a combination as set forth in claim 17,
the range of energies in the x-rays being between approximately 10.6 Mev and approximately 13.0 Mev.

19. In a combination as set forth in claim 12,
the x-ray means constituting a converter target of bremsstrahlung x-rays and the indicating means constituting a scintillation counter.

20. In combination for determining the presence of explosives by measuring the concentration of nitrogen in an object,
means for producing an energy in a first form,
means responsive to the energy in the first form for producing energy in a second form in a particular range of energy intensities in which nitrogen, among other commonly appearing elements, is preferentially responsive to the energy intensities in the particular range to produce energy in a third form, the means for producing the energy in the second form being disposed to direct the energy in the second form to the object, the energy in the second form constituting x-rays with photons in the x-rays, and means responsive to the energy in the third form for indicating the concentration of the nitrogen in the object, the energy in the third form constituting annihilation photons produced when the photons in the x-rays interact with the nuclei of the nitrogen.

21. In a combination as set forth in claim 20,
the indicating means being disposed relative to the energies in the first, second and third forms to be responsive preferentially to the energy in the third form.

22. In a combination as set forth in claim 21,
means for activating the indicating means preferentially during the production of the energy in the third form.

23. In a combination as set forth in claim 22,
the means for producing the energy in the second form constituting a bremsstrahlung converter target in which energy is produced in a range of energy intensities between approximately 10.6 Mev and approximately 13.0 Mev and the nitrogen in the object being responsive to the energy in the second form at an energy level of at least approximately 10.6 Mev to produce the energy in the third form.

24. A method of determining the presence of explosives by measuring the concentration of nitrogen in an object, including the steps of:
directing energy in a first form to a converter target to obtain the production of energy in a second form in a range of energy intensities in which nitrogen is responsive, to the substantial exclusion of other commonly appearing elements, to obtain the production of energy in a third form, and
indicating the concentration of the nitrogen in the object in accordance with the amount of energy produced in the third form,
the energy in the first form constituting electrons,
the energy in the second form constituting x-rays with photons in the x-rays, for nuclear interreaction of the photons with the nuclei in the nitrogen to obtain the production of annihilation photons, the annihilation photons constituting the energy i the third form.

25. A method as set forth in claim 21 wherein
the energy in the second form is in a range of levels between approximately 10.6 Mev and approximately 13.0 Mev and the nitrogen in the object is response to the energy in the second form at an energy level of at least approximately 10.6 Mev.

26. A method as set forth in claim 24 wherein
the indication of the energy in the third form is at a position where the energy in the first form and the energy in the second form have substantially no effect on such indication.

27. A method as set forth in claim 21 wherein
the object is moved in a particular direction relative to the energy in the first form and wherein
the detection of the energy in the third form is downstream in the particular direction from the position at which the energy is directed in the first form.

28. A method as set forth in claim 25 wherein
the beam of electrons is provided only periodically and the detection of the energy in the third form is made substantially only during particular times relative to the times that the beam of electron is provided periodically.

29. A method as set forth in claim 27 wherein the energy in the second form has a range of energy levels between approximately 10.6 Mev and approximately 13.0 Mev and the energy is produced in the third form from the nitrogen in the object preferentially when the energy in the second form has a level of at least approximately 10.6 Mev.

30. A method as set forth in claim 25 wherein
shielding is provided for the detection of the energy in the third form to insure that the energy in the third form is detected only from the nitrogen in the object.

31. A method of indicating the presence of explosives by measuring the amount of nitrogen in an object, including the steps of:
   providing a beam of electrons in a first direction,
   intercepting the electron beam to obtain the production of x-rays, with photons in the x-rays, in an energy range in which nitrogen is preferentially responsive among other commonly appearing elements, the photons in the x-rays providing a nuclear interreaction with the nuclei in the nitrogen to obtain the production of annihilation photons,
   disposing the object relative to the x-rays to obtain the production of the annihilation photons, and
   detecting the annihilation photons to provide an indication of the concentration of the nitrogen in the object.

32. In combination for determining the presence of explosives by measuring the relative concentration of nitrogen in an object,
   means for producing x-rays, with photons in the x-rays, in a range of intensities substantially only between approximately 10.6 Mev and 13.0 Mev and for directing the x-rays toward the object to obtain the nuclear interreaction of the photons in the x-rays with the nuclei in the nitrogen to obtain the production of annihilation photons,
   means for gating the production of the x-rays in a timed pulse to obtain the production of the annihilation photons in the timed pulse, and
   means responsive to the timed pulse of the annihilation photons for indicating the concentration of the nitrogen in the object.

33. In a combination as set forth in claim 32,
   means disposed relative to the x-ray producing means and the indicating means for insuring that the indicating means is responsive only to the x-rays from the x-ray producing means to indicate the concentration of the nitrogen in the object.

34. In a combination as recited in claim 33,
   means for gating the responsive of the indicating means to the pulses of the annihilation photons in a particular timed relationship with the pulsed production of the x-rays by the x-ray producing means.

35. In a combination as set forth in claim 32,
   means for providing a hollow shielded enclosure, and
   means for moving the object in a particular direction through the hollow shielded enclosure,
   the x-ray producing means being disposed at a first position in the hollow shielded enclosure, and
   the indicating means being disposed at a second position in the hollow shielded enclosure, the second position being displaced from the first position in the particular direction.

36. In a combination as set forth in claim 35,
   means disposed relative to the x-ray producing means and the indicating means for insuring that the indicating means is responsive only to the annihilation photons to indicate the concentration of the nitrogen in the object.

37. In a combination as recited in claim 36,
   means for gating the response of the indicating means to the pulses of the annihilation photons in a particular timed relationship with the pulsed production of the x-rays by the x-ray producing means.

* * * * *